United States Patent
Feng et al.

(10) Patent No.: US 7,078,909 B2
(45) Date of Patent: Jul. 18, 2006

(54) FLOW-THROUGH CONDUCTIVITY SENSOR

(75) Inventors: Chang-Dong Feng, Long Beach, CA (US); Barry Benton, Orange, CA (US); Behzad Rezvani, Anaheim, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 10/735,543

(22) Filed: Dec. 12, 2003

(65) Prior Publication Data

US 2005/0127919 A1    Jun. 16, 2005

(51) Int. Cl.
*G01N 27/08* (2006.01)
*G01R 15/18* (2006.01)
*G01F 1/64* (2006.01)

(52) U.S. Cl. ............... 324/439; 324/127; 324/701; 73/861.11

(58) Field of Classification Search ............... 324/439, 324/126, 127, 695, 445, 446, 693, 430, 701; 73/861.08, 861.11, 861.12
See application file for complete search history.

(56) References Cited

U.S. PATENT DOCUMENTS

| | | | |
|---|---|---|---|
| 2,004,569 A | 6/1935 | Davis, Jr. | |
| 3,286,522 A * | 11/1966 | Cushing | 73/861.11 |
| 3,387,209 A * | 6/1968 | Eames et al. | 324/693 |
| 3,404,336 A * | 10/1968 | Rosenthal | 324/445 |
| 3,924,175 A | 12/1975 | Wilson | 324/30 |
| 3,936,729 A | 2/1976 | Winslow et al. | 324/30 |
| 3,980,946 A * | 9/1976 | Fleury | 324/445 |
| 4,100,491 A * | 7/1978 | Newman et al. | 324/446 |
| 4,751,466 A | 6/1988 | Colvin et al. | 324/449 |
| 5,077,525 A | 12/1991 | West et al. | 324/445 |
| 5,157,332 A | 10/1992 | Reese | 324/445 |
| 5,367,911 A * | 11/1994 | Jewell et al. | 73/861.08 |
| 5,438,257 A * | 8/1995 | Berkcan | 324/117 R |
| 5,455,513 A * | 10/1995 | Brown et al. | 324/445 |
| 5,708,363 A | 1/1998 | Yates et al. | 324/442 |
| 6,359,449 B1 | 3/2002 | Reining et al. | 324/692 |
| 2002/0140564 A1 * | 10/2002 | Danyluk et al. | 340/603 |

FOREIGN PATENT DOCUMENTS

FR    2607249 A1 *    5/1988

OTHER PUBLICATIONS

"Conductivity Sensor Advances," Bob Langie, Application Note, Dec. 2000, p. 8.
"Endurance Conductivity Sensors," Product Data Sheet, Model 400 Series, Emerson Process Management, Jun. 2003.
"Model 242—Flow-Through Toroidal Conductivity Sensor," Emerson Process Management, 2003.

* cited by examiner

*Primary Examiner*—Anjan Deb
(74) *Attorney, Agent, or Firm*—Westman, Champlin & Kelly, P.A.

(57) ABSTRACT

An improved flow-through conductivity sensor is provided. The sensor includes a current return path that has a current return conductor. At least one toroid of the sensor is removed from the flow path and configured to interact with the current return conductor to provide an indication of conductivity. Additional aspects of the invention include disposing a pair of toroids about the current return conductor; disposing a toroid about the current return conductor and configuring the toroid as a transformer.

13 Claims, 8 Drawing Sheets

FLOW-THROUGH CONDUCTIVITY SENSOR

FIELD OF THE INVENTION

The present invention is related to devices and systems that measure conductivity. More particularly, the present invention relates to flow-through type conductivity sensors.

BACKGROUND OF THE INVENTION

Conductivity measurement sensors are well known in the art and are used to measure the conductivity of a fluid, such as a liquid or a dispersion of solids suspended in a liquid. Conductivity sensors are often used to investigate the properties of electrolytes in solution, such as the degree of disassociation, the formation of chemical complexes, and hydrolysis. The conductivity of a fluid may also be used to measure a wide variety of other parameters, such as the amount of contaminants in drinking water and a measure of chemical concentrations in industrial process streams. Applications such as these involve the determination of conductivities in many different physical environments.

Toroidal conductivity sensors generally include two toroidal coils. The first coil is electrically excited by an alternating current source to generate a changing magnetic field. The changing magnetic field induces an electrical current in the liquid. In electrolytic solutions, the mechanism of electrical current transfer is dependent on ions. The magnitude of the induced current is indicative of the conductivity of the liquid. The second coil detects the magnitude of the induced current. Typically, toroidal conductivity sensors are best suited for use in processes where conventional conductivity sensors, such as those with electrodes exposed to the measured solution, would corrode or become foul.

One example of a toroidal conductivity sensor is sold under the trade designation Model 242 available from the Rosemount Analytical, Incorporated Division of Emerson Process, which division is located in Irvine, Calif. The Model 242 sensor is designed to be installed easily into process piping between mounting flanges. As a flow-through conductivity sensor, the Model 242 is not sensitive to flow rate or direction and it does not obstruct the flow of process fluid. Typically, a flow-through conductivity sensor, such as the Model 242 is electrically coupled to a compatible instrument such as instrument models 54eC, 1055, 3081T, 4081T and 5081T, all of which are available from the Rosemount Analytical, Incorporated Division of Emerson Process.

Toroidal conductivity sensors of the prior art have generally performed well. One limitation of such sensors, however, has been that when sensors are offered for different pipe sizes, different sized toroids must be manufactured to accommodate the various pipe sizes. Once a company offers three or four pipe sizes as well as toroids having different winding counts for each pipe size, the sheer number of different toroids that must be manufactured grows quickly. This tends to drive up manufacturing costs since the individual lots of toroids are relatively smaller. Providing a toroidal-type conductivity sensor that could use standardized toroids would allow manufacturing of such toroids to be done on a much larger scale and thus the component cost of the toroid reduced thereby also reducing costs of the final unit.

SUMMARY OF THE INVENTION

An improved flow-through conductivity sensor is provided. The sensor includes a current return path that has a current return conductor. At least one toroid of the sensor is removed from the flow path and configured to interact with the current return conductor to provide an indication of conductivity. Additional aspects of the invention include disposing a pair of toroids about the current return conductor; disposing a toroid about the current return conductor and configuring the toroid as a transformer.

DETAILED DESCRIPTION OF THE PREFERRED EMBODIMENTS

Figure 1:
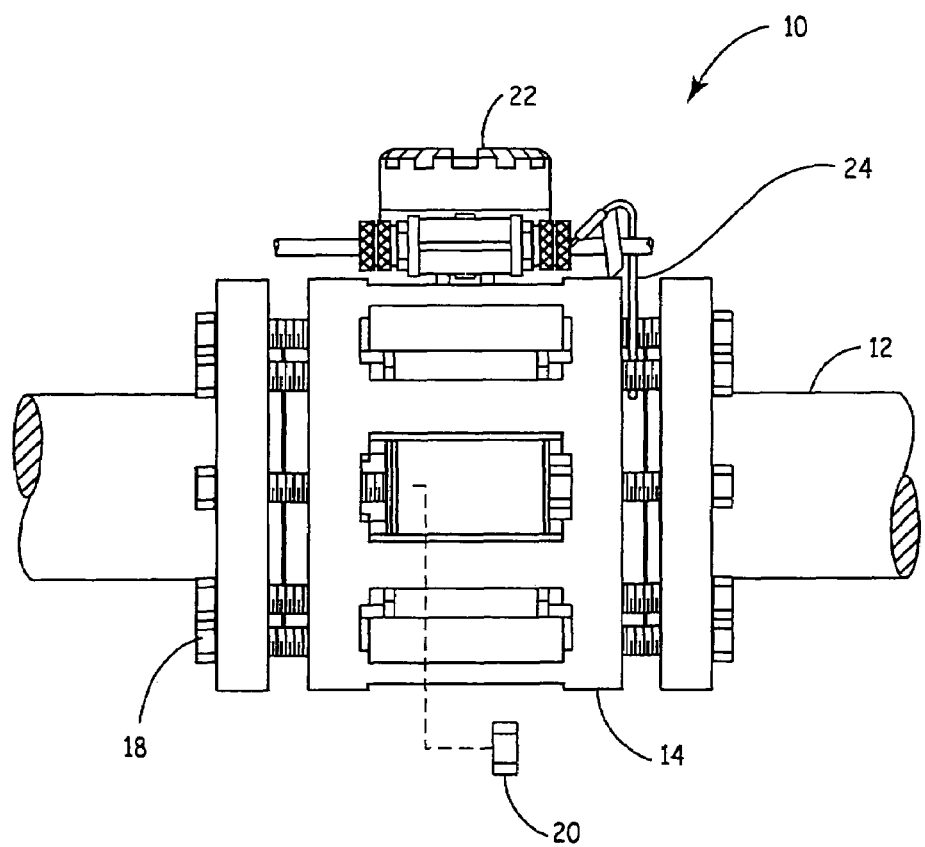
FIGS. 1 and 2 are side elevation and perspective views, respectively, of a flow-through conductivity sensor in accordance with the prior art.
Figure 2:
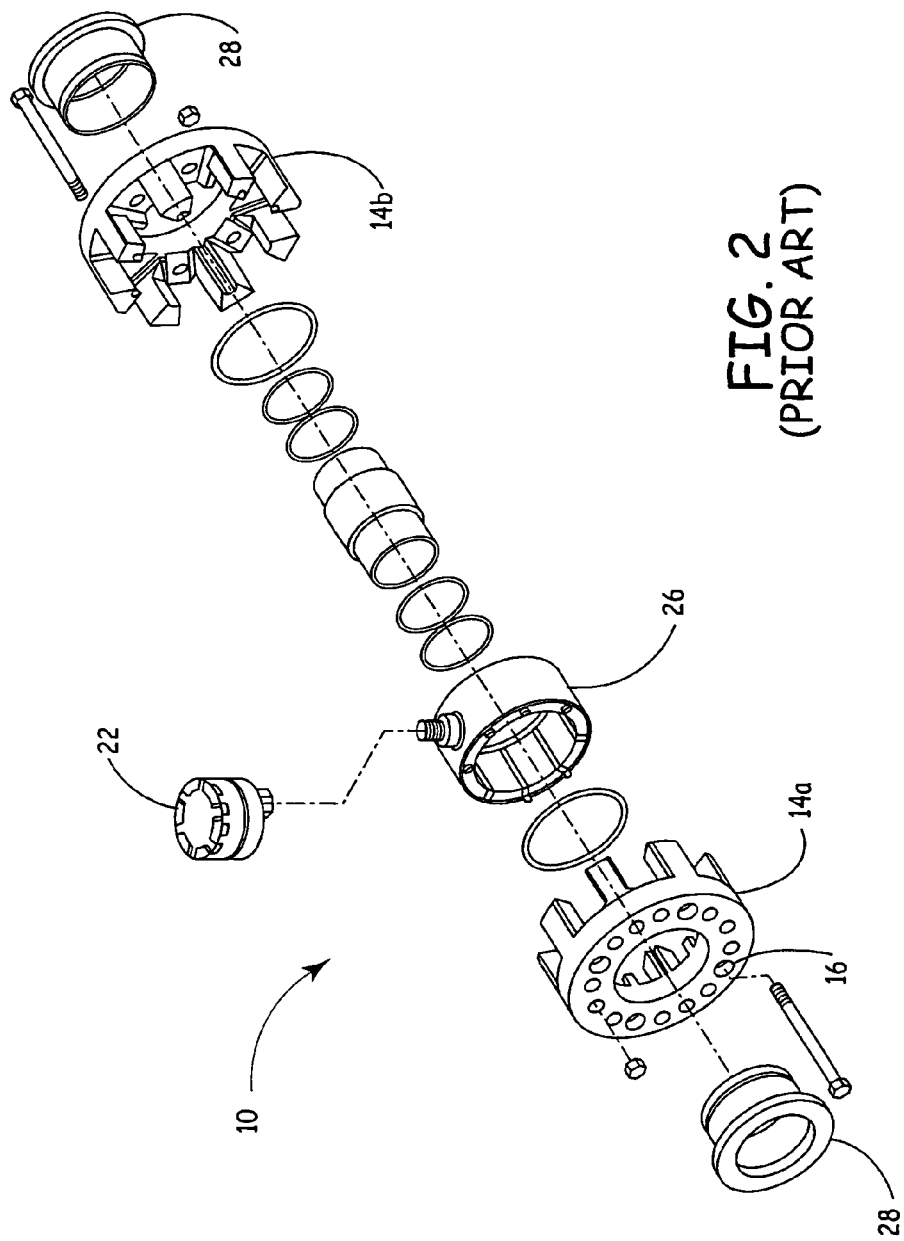

FIGS. 1 and 2 are side elevation and perspective views, respectively, of a flow-through conductivity sensor in accordance with the prior art. Sensor 10 is adapted to mount to process piping 12 in order to measure conductivity of process fluid flowing therethrough. Sensor 10 includes body 14 which is generally a two-part construction from halves 14a and 14b (illustrated in FIG. 2). A number of holes 16 within each of the halves 14a, 14b are sized to receive mounting bolts 18 and allow the body to be fixed to pipe flanges using mounting bolts 18 and suitable fasteners 20. Junction box 22 is generally fixed to the top of sensor 10 and includes any suitable wiring terminations and connections, as may be appropriate. Since it is generally known that conductivity can vary as a function of temperature, sensor 10 generally includes a temperature sensitive device 24 that is adapted to provide an indication of process fluid temperature flowing through sensor 10 such that the conductivity measurement can be compensated for temperature.

Referring specifically to FIG. 2, toroid housing 26 is disposed between each of halves 14a and 14b and contains both the drive and receive toroid. As illustrated, toroid housing 26 is sized such that the process fluid flows through the toroid housing 26 and thus through both the drive toroid and the receive toroid. FIG. 2 also shows a pair of contacting rings 28 which are generally adapted to make electrical contact with the fluid flowing therethrough. These contacting rings 28 are also electrically coupled to body 14 which itself is generally conductive. Accordingly, the combination of a pair of contacting rings 28 and the metal housing of the sensor itself provide a current return path for the current excited in the fluid as a result of operation of the drive toroid.

Figure 3:
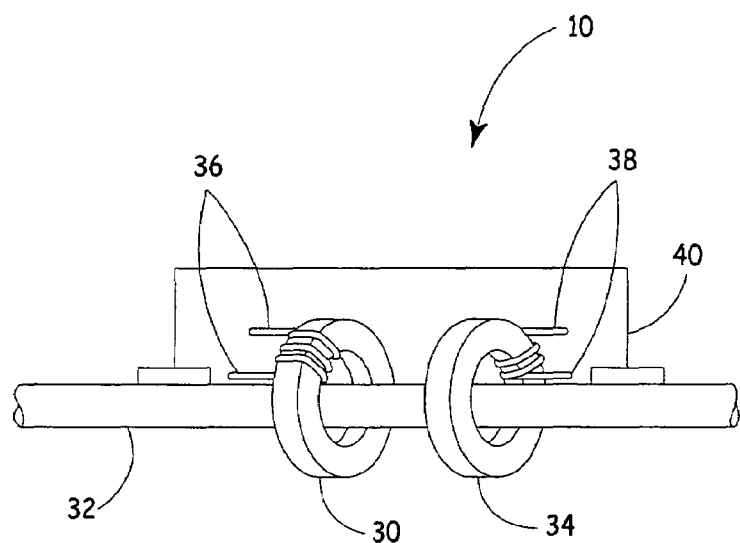
FIG. 3 illustrates, diagrammatically, the operation of the drive toroid, the receive toroid, and the current return path.

FIG. 3 illustrates, diagrammatically, the operation of the drive toroid, the receive toroid, and the current return path formed by virtue of the contacting rings 28 and the conductive housing 14 of sensor 10. Drive toroid 30 is disposed about process fluid flow path 32. Receive toroid 34 is also disposed about flow path 32. The application of an alternating current to conductors 36, wound about drive toroid 30, generates a changing magnetic field that induces a current within the conductive process fluid within flow path 32. This current is detected by receive toroid 34 at conductors 38 which are wound about receive toroid 34 and coupled to suitable detection circuitry (not shown). In order to create a closed circuit, current return path 40 is provided. In the prior art, current return path 40 is generally formed by conductive rings being electrically coupled to a conductive sensor housing. As illustrated in FIG. 3, prior art toroidal flow-through sensors provide both toroids (drive and receive) about the flow path. As set forth above, the flow path may be a pipe of varying sizes depending on the application. Accordingly, design and manufacture of the flow-through sensor is somewhat customized depending on the size of the flow path since toroids must be designed that can fit around the flow path while still effectively coupling the magnetic fields to the flow path.

Many embodiments of the present invention will be described with respect to process piping that has a non-conductive inner surface. However, embodiments of the present invention are equally practicable with process piping that has a conductive inner surface. Suitable electrodes for these applications are described in greater detail with respect to FIGS. 7 and 8.

Figure 4:
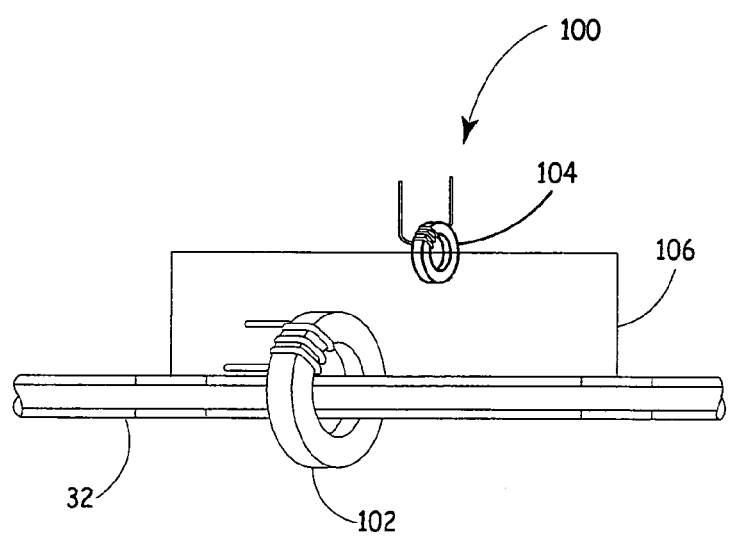
FIG. 4 is a diagrammatic view of a flow-through conductivity sensor in accordance with an embodiment of the present invention.

FIG. 4 is a diagrammatic view of a flow-through conductivity sensor in accordance with an embodiment of the present invention. In accordance with one broad aspect, sensor 100 is similar to sensors of the prior art with two important exceptions. First, at least one of toroids 102, 104 is removed from the flow path. Specifically, toroid 104 has been disposed about current return conductor 106. Current return conductor 106 also differs from current return paths of the prior art in that it is actually a conductor, such as a wire. One example of current return path 106 might include a pair of contact rings, such as contact rings 28, but which rings 28 are then electrically isolated from the conductive sensor body. An electrical conductor, such as a wire, is then electrically coupled to each of the contact rings 28 in order to force all return current through the conductor. This configuration then allows a toroid 104 to be disposed about the conductor to interact with the current. Embodiments of the present invention include toroid 102 being a drive toroid and toroid 104 being a receive toroid; or toroid 104 being a drive toroid and toroid 102 being a receive toroid. This configuration is an improvement over the prior art in that at least one toroid can be formed with a standardized size (particularly toroid 104 illustrated in FIG. 4). Those skilled in the art will appreciate that the construction of current return path 106 can be done in any suitable manner in which a pair of electrical conductors are brought into contact with the process fluid and where such conductors are coupled to one another through an electrical conductor of suitable size to have a toroid disposed thereabout. For example, when the process piping itself is non-conductive, the connection of the electrodes to the process pipe can be realized by using built-in pipe thread or flange of the electrodes. Thus, the electrodes can take any form as long as conductive electrode material is brought into contact with the process fluid.

Figure 5:
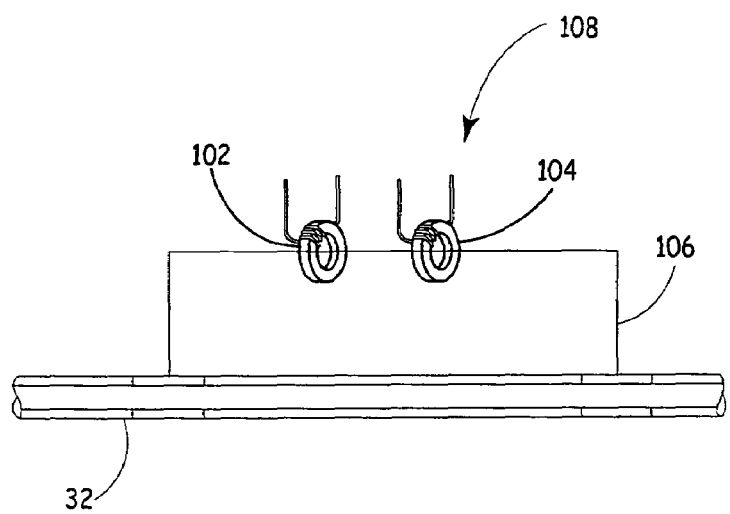
FIG. 5 is a diagrammatic view of a flow-through conductivity sensor in accordance with another embodiment of the present invention.

FIG. 5 is a diagrammatic view of a flow-through toroidal conductivity sensor in accordance with another embodiment of the present invention. The embodiment illustrated in FIG. 5 extends the benefits of the present invention by disposing both toroids about the current return path. Thus, one of toroids 104, 110 is a drive toroid while the other is a receive toroid. In this embodiment, both toroids 104 and 110 can be constructed from a standardized design that does not vary as the pipe diameter varies. Accordingly, toroids 104 and 110 can be more cost effectively mass-produced while still providing benefits of non-contact conductivity measurement for sensor 108.

Figure 6:
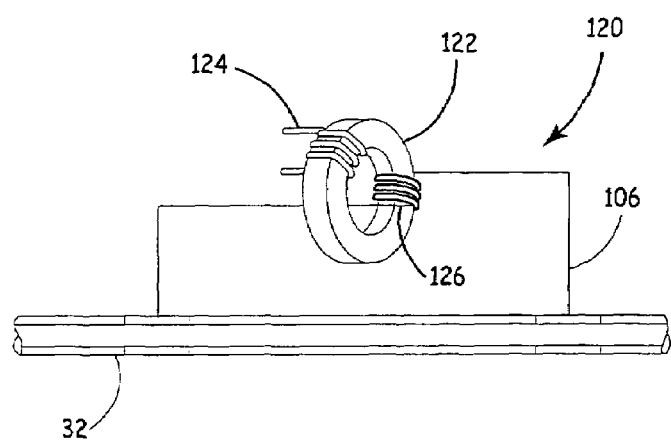
FIG. 6 is a diagrammatic view of a flow-through toroidal conductivity sensor in accordance with another embodiment of the present invention.

FIG. 6 is a diagrammatic view of a flow-through toroidal conductivity sensor in accordance with another embodiment of the present invention. Sensor 120 includes a single toroid configured to act as a transformer. Accordingly, toroid 122 includes a first winding 124; and a second winding 126 electrically coupled in series with current return path 106. Sensor 120 is a hybrid design in the sense that it allows a hybrid form of measurement of conductivity by sensing the impedance across winding 124. Sensor 120 provides hybrid measurement of conductivity because the measurement is somewhat isolated from the current return path, but the transformer-configured toroid is disposed at the sensor and maintains some of the benefits of toroidal conductivity measurement. This configuration may provide impedance matching and/or isolation required to read the conductivity using direct impedance measurement techniques. In other embodiments, coupling the electrodes directly to suitable detection circuitry may allow for direct conductivity measurement. Preferably, multiple measurement regimes (toroidal, hybrid and direct) can be selected with an electric switch (not shown).

The description with respect to the embodiments illustrated in FIGS. 4–6 disclose sensors in which current flow within the process fluid is generated and sensed without having two or more toroids disposed about the process fluid flow path. The embodiments differ somewhat in the manner in which current flow is generated and/or sensed.

Figure 7:
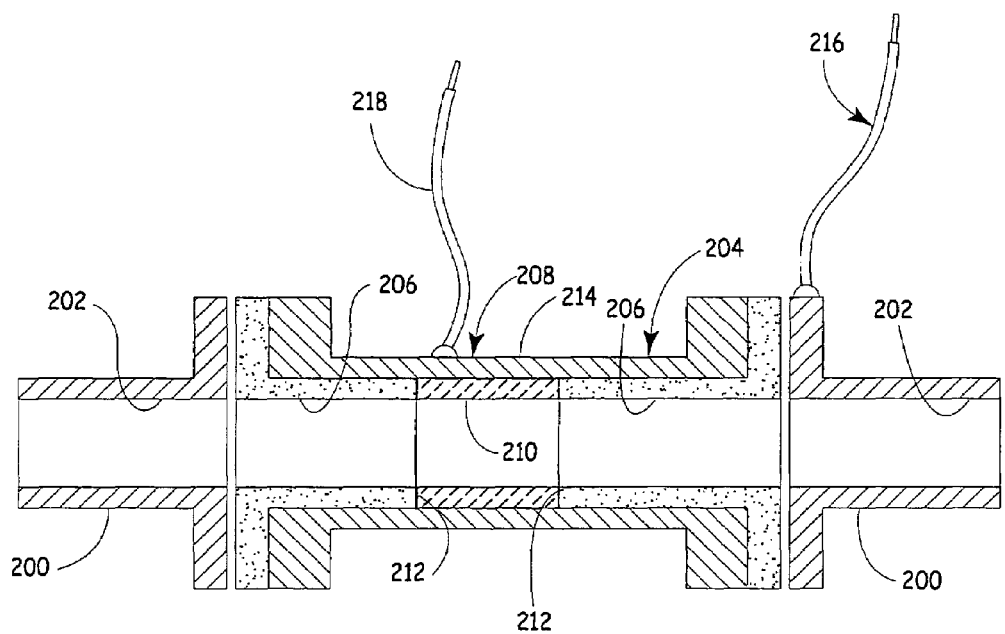
FIG. 7 is a diagrammatic view of a pair of electrodes usable with embodiments of the present invention when process piping has a conductive inner surface.

FIG. 7 is a diagrammatic view of a pair of electrodes usable with embodiments of the present invention when process piping has a conductive inner surface. Process piping 200 has a conductive inner surface 202. Sensor pipe 204, which is a part of the flow-through conductivity sensor, has a non-conductive liner 206 that extends inwardly from each end of sensor pipe 204. Liner 206 isolates sensor pipe 204 from conductive process piping 200. A first electrode 208 is formed by a contact ring 210 disposed within pipe 204 beyond the ends 212 of liner 206. Accordingly, ring 210 contacts process fluid flowing through pipe 204. Ring 210 is electrically coupled to conductive sensor pipe portion 214, such that electrical access to process fluid flowing through pipe 204 can be made through portion 214 and ring 210.

A second electrode is formed by electrically coupling to one of the conductive process pipes 200. Accordingly, a pair of electrodes 216, 218 can be formed relatively easily to facilitate operation of embodiments of the present invention with conductive process piping.

Figure 8:
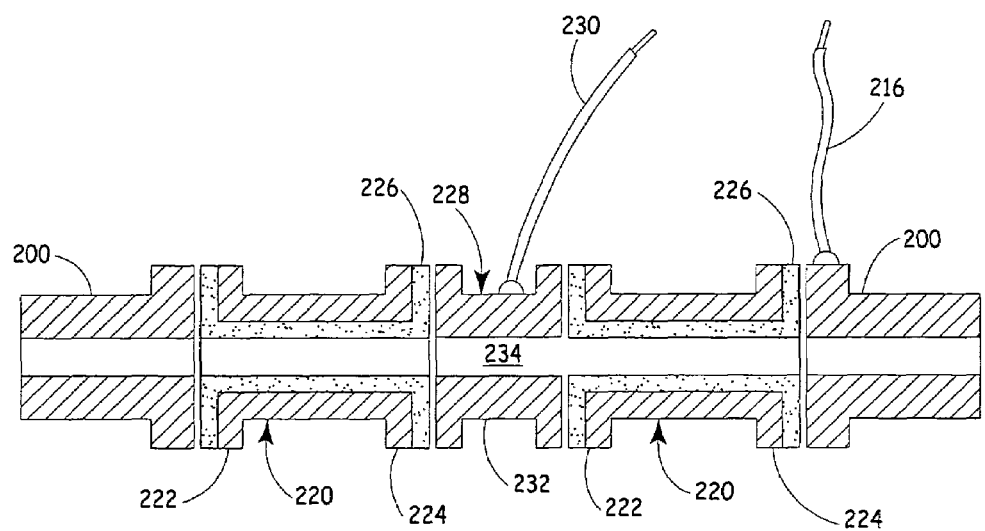
FIG. 8 is a diagrammatic view of a pair of electrodes formed with commercially available flange pipe in accordance with embodiments of the present invention.

FIG. 8 is a diagrammatic view of a pair of electrodes formed with commercially available flange pipe in accordance with embodiments of the present invention. FIG. 8 bears some similarities to FIG. 7 and like components are numbered similarly. Electrode 216 is the same as in FIG. 7. In contrast to FIG. 7, a pair of commercially available metal pipes 220 are each coupled to conductive process piping 200. Each of pipes 220 includes a pair of flanges 222, 224 and an insulating liner 226 that extends from each end of the pipe 220 throughout the interior of the pipe. Conductive pipe 228 is positioned between each of pipes 220 and is electrically isolated from process piping 200 by virtue of insulating liners 226 on either side of pipe 228. An electrode 230 is formed using conductive pipe 228, since electrically coupling to the outside 232 of pipe 228 will allow electrical access to process fluid flowing through interior 234.

Embodiments of the present invention generally remove at least one of a pair of toroids from a process fluid flow path. This allows greater standardization in manufacture of toroids for flow-through sensors. Disposing both toroids about a current return path provides further advantages. Additionally, configuring a toroid as a transformer right at the flow-through sensor (illustrated in FIG. 6) is believed to provide a system that is more tolerant of the cabling used to connect the sensor to associated instrumentation.

Although the present invention has been described with reference to preferred embodiments, workers skilled in the art will recognize that changes may be made in form and detail without departing from the spirit and scope of the invention. Embodiments of the present invention are usable with non-conductive process piping as well as conductive process piping.

What is claimed is:

1. A flow-through conductivity sensor, the sensor comprising:
    a flow conduit;
    first and second electrodes disposed relative to the flow conduit to contact process fluid proximate the conduit and convey an electrical current between the first and second electrodes through the process fluid;
    a current return conductor coupled to the first and second electrodes; and
    at least one toroid arranged to interact with the current return conductor to measure current flowing between the first and second electrodes through the process fluid provide an indication of process fluid conductance.

2. The sensor of claim 1, wherein the at least one toroid is disposed about the current return conductor.

3. The sensor of claim 2, and further comprising:
    a second toroid disposed about the current return conductor; and
    wherein one toroid is a drive toroid and the other toroid is a detect toroid.

4. The sensor of claim 2, wherein the at least one toroid is configured as a transformer.

5. The sensor of claim 2, wherein the at least one toroid has a pair of windings, and one of the pair of windings is in series with the current return conductor.

6. The sensor of claim 1, wherein at least one of the first and second electrodes is a contact ring.

7. The sensor of claim 1, wherein one of the first and second electrodes includes a conductive process pipe.

8. The sensor of claim 7, wherein the other of the first and second electrodes includes a contact ring.

9. The sensor of claim 7, wherein the other of the first and second electrodes includes a metal pipe disposed between a pair of insulating pipes, wherein each insulating pipe includes insulating ends and an insulating liner.

10. A method of measuring conductivity of a process fluid in a flow conduit, the method comprising:
    contacting the process fluid with first and second electrodes coupled together by a current return path;
    generating an electrical current between the first and second electrodes in the process fluid with a drive toroid; and
    measuring current through the current return path, the measured current through the current return path being indicative of the conductivity.

11. The method of claim 10, wherein measuring includes coupling a receive toroid to the current return path.

12. The method of claim 10, wherein generating includes coupling the drive toroid to the current return path.

13. The method of claim 10, wherein measuring includes directly measuring impedance of a toroid coupled to the current return path.

* * * * *